United States Patent
Collier et al.

(10) Patent No.: US 11,225,445 B2
(45) Date of Patent: Jan. 18, 2022

(54) PROCESS FOR THE PRODUCTION OF TRANS-1-CHLORO-3,3,3-TRIFLUOROPROPENE

(71) Applicant: ARKEMA FRANCE, Colombes (FR)

(72) Inventors: Bertrand Collier, Pierre-Benite (FR); Anne Pigamo, Pierre-Benite (FR); Nicolas Brusadelli, Pierre-Benite (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 17/260,146

(22) PCT Filed: Jul. 16, 2019

(86) PCT No.: PCT/FR2019/051776
§ 371 (c)(1),
(2) Date: Jan. 13, 2021

(87) PCT Pub. No.: WO2020/016515
PCT Pub. Date: Jan. 23, 2020

(65) Prior Publication Data
US 2021/0317053 A1    Oct. 14, 2021

(30) Foreign Application Priority Data
Jul. 18, 2018 (FR) ...................................... 1856644

(51) Int. Cl.
*C07C 17/20* (2006.01)
*C07C 21/18* (2006.01)
*C07C 17/25* (2006.01)

(52) U.S. Cl.
CPC ............ *C07C 17/206* (2013.01); *C07C 17/25* (2013.01); *C07C 21/18* (2013.01); *C07B 2200/09* (2013.01)

(58) Field of Classification Search
CPC ....... C07C 17/25; C07C 21/18; C07C 17/206; C07B 2200/09
See application file for complete search history.

(56) References Cited

U.S. PATENT DOCUMENTS

| | | | |
|---|---|---|---|
| 5,877,359 A | 3/1999 | Elsheikh | |
| 6,166,274 A | 12/2000 | Chen et al. | |
| 9,255,045 B2 | 2/2016 | Pigamo et al. | |
| 9,643,903 B2 | 5/2017 | Pokrovski et al. | |
| 2004/0033892 A1 | 2/2004 | Bonnet et al. | |
| 2015/0197467 A1 | 7/2015 | Pigamo et al. | |

FOREIGN PATENT DOCUMENTS

WO    0181353 A1    11/2001

OTHER PUBLICATIONS

ISA/EP; International Search Report and Written Opinion for International Patent Application No. PCT/FR2019/051176 dated Sep. 11, 2019, 10 pages.

*Primary Examiner* — Jafar F Parsa
(74) *Attorney, Agent, or Firm* — NK Patent Law

(57) ABSTRACT

A process for the production of trans-1-chloro-3,3,3-trifluoropropene comprises the steps of: i) providing a reactor comprising a cover, a bottom, sidewalls connecting said bottom and said cover, at least one reagent supply line and at least one line for drawing off the products formed, said reactor further containing a liquid phase A; ii) providing a stream B comprising hydrofluoric acid heated to a temperature T1 of from 100° C. to 170° C. and providing a stream C comprising 1,1,3,3-tetrachloropropene and/or 1,3,3,3-tetrachloropropene; stream B and stream C supplying said reactor via said at least one reagent supply line; iii) reacting, in liquid phase A, stream B with stream C to form a stream D comprising trans-1-chloro-3,3,3-trifluoropropene. Step iii) is carried out at a temperature T2 of between 50° C. and 110° C., and the temperature difference between temperature T1 and temperature T2 is greater than 30° C.

11 Claims, No Drawings

PROCESS FOR THE PRODUCTION OF TRANS-1-CHLORO-3,3,3-TRIFLUOROPROPENE

CROSS-REFERENCE TO RELATED APPLICATIONS

This application is a U.S. National Stage application of International Patent Application No. PCT/FR2019/051776, filed on Jul. 16, 2019, which claims the benefit of French Patent Application No. 1856644, filed on Jul. 18, 2018.

TECHNICAL FIELD OF THE INVENTION

The present invention relates to the production of hydrochlorofluoroolefins. More particularly, the present invention relates to the production of 1-chloro-3,3,3-trifluoropropene.

TECHNOLOGICAL BACKGROUND OF THE INVENTION 3,3,3-Trifluoro-1-chloropropene, or alternatively 1-chloro-3,3,3-trifluoropropene (HCFO-1233zd), exists in the form of two isomers: the cis isomer, namely Z-3,3,3-trifluoro-1-chloropropene (HCFO-1233zdZ), and the trans isomer, namely E-3,3,3-trifluoro-1-chloropropene (HCFO-1233zdE). They have different boiling points of, respectively, 18.5° C. for the trans compound and 39.5° C. for the cis compound.

Fluids based on E-3,3,3-trifluoro-1-chloropropene (HCFO-1233zdE) have found numerous applications in varied industrial fields, in particular as heat transfer fluids, propellants, foaming agents, blowing agents, gaseous dielectrics, monomers or polymerization media, support fluids, abrasive agents, drying agents, and fluids for energy production units.

The manufacture of HCFO-1233zdE is accompanied by a multitude of by-products having a boiling point close to HCFO-1233zdE. This results in purification steps which are relatively complex and costly. The difficulties encountered during the purification of HCFO-1233zdE generally entail an appreciable loss of target product. In addition, the by-products may form azeotropic compositions with the HCFO-1233zdE, making separation by simple distillation very difficult, or even impossible.

U.S. Pat. No. 5,877,359 discloses a process for preparing HCFO-1233zdE from 1,1,3,3-tetrachloropropene in liquid phase and in the absence of catalyst. U.S. Pat. No. 9,643,903 also discloses a process for the fluorination of 1,1,3,3-tetrachloropropene in liquid phase and in the absence of catalyst, in an HF-rich medium. Also known from U.S. Pat. No. 9,255,045 is a process for the fluorination of 1,1,3,3-tetrachloropropene to give 1-chloro-3,3,3-trifluoropropene.

Generally, the fluorination reaction is carried out at a temperature requiring the reactor to be heated to a temperature clearly higher than the targeted reaction temperature. The high temperature of the reactor walls locally generates an increase in the production of by-products such as cis-1-chloro-3,3,3-trifluoropropene or the production of overfluorinated products such as 1,1,1,3,3-pentafluoropropane or 1,3,3,3-tetrafluoropropene.

There is a need for an efficient process for the production of trans-1-chloro-3,3,3-trifluoropropene which minimizes the production of by-products or overfluorinated products.

SUMMARY OF THE INVENTION

The applicant has surprisingly observed that the preheating of the starting raw material, in particular the preheating of hydrofluoric acid, to a temperature clearly higher than the reaction temperature makes it possible to limit the heating of the reactor.

The present invention provides a process for the production of trans-1-chloro-3,3,3-trifluoropropene, comprising the steps of:

i) providing a reactor comprising a cover, a bottom, sidewalls connecting said bottom and said cover, at least one reagent supply line and at least one line for drawing off the products formed, said reactor further containing a liquid phase A;

ii) providing a stream B comprising hydrofluoric acid heated to a temperature T1 of from 100° C. to 170° C. and providing a stream C comprising 1,1,3,3-tetrachloropropene and/or 1,3,3,3-tetrachloropropene; said stream B and said stream C supplying said reactor via said at least one reagent supply line;

iii) reacting, in said liquid phase A, said stream B with said stream C in order to form a stream D comprising trans-1-chloro-3,3,3-trifluoropropene;

characterized in that step iii) is carried out at a temperature T2 of between 50° C. and 110° C., and the temperature difference, in absolute value, between said temperature T1 and said temperature T2 is greater than or equal to 30° C.

According to one preferred embodiment, said reactor also comprises heating means capable of heating said liquid phase A; the temperature of said heating means is the temperature T3; said temperature T3 is higher than the temperature T2 and said temperature T3 is less than 120° C.

According to one preferred embodiment, said liquid phase A provided in step i) is heated prior to the implementation of step iii) to a temperature T4 of between 50° C. and 110° C.; preferably, the temperature T4 is equal to the temperature T2.

According to a preferred embodiment, said liquid phase A is a liquid phase low in HF.

According to one preferred embodiment, said liquid phase low in HF is a liquid phase comprising less than 15% by weight of HF, advantageously less than 10% by weight of HF, preferably less than 8% by weight of HF, more preferentially less than 6% by weight of HF, in particular less than 5% by weight of HF, more particularly less than 4% by weight of HF, favorably less than 2% by weight of HF, based on the total weight of said liquid phase.

According to one preferred embodiment, the temperature T2 is between 60° C. and 105° C., preferably between 70° C. and 100° C., more preferentially between 80° C. and 100° C., in particular between 85° C. and 95° C., more particularly between 88° C. and 92° C.

According to one preferred embodiment, the temperature T1 is between 120° C. and 170° C., in particular between 125° C. and 165° C., more particularly between 125° C. and 155° C.

According to one preferred embodiment, the temperature T3 is less than 115° C., preferably less than 110° C., more preferentially less than 105° C., in particular less than 100° C.

According to one preferred embodiment, said stream D also comprises at least one of the by-products selected from the group consisting of 1,1,1,3,3-pentafluoropropane, cis/trans-1,3,3,3-tetrafluoropropene and cis-1-chloro-3,3,3-trifluoropropene; and the total molar content of said at least one of the by-products is less than 5 mol % in said stream D.

According to one preferred embodiment, the molar content of trans-1-chloro-3,3,3-trifluoropropene in said stream D is greater than 95 mol %.

According to one preferred embodiment, step iii) is carried out at a pressure of between 5 and 20 bara, preferably between 10 and 18 bara.

DETAILED DESCRIPTION OF THE INVENTION

The present invention relates to a process for the production of trans-1-chloro-3,3,3-trifluoropropene. In particular, the present process is carried out in a reactor comprising a cover, a bottom, sidewalls connecting said bottom and said cover, at least one reagent supply line and at least one line for drawing off the products formed.

In addition, said reactor contains a liquid phase A. Said liquid phase A is a liquid phase low in HF or a liquid phase rich in HF.

Said liquid phase A low in HF is a liquid phase comprising less than 15% by weight of HF, advantageously less than 10% by weight of HF, preferably less than 8% by weight of HF, more preferentially less than 6% by weight of HF, in particular less than 5% by weight of HF, more particularly less than 4% by weight of HF, preferably less than 2% by weight of HF, based on the total weight of said liquid phase.

Said liquid phase A rich in HF is a liquid phase comprising more than 20% by weight of HF, advantageously more than 25% by weight of HF, preferably more than 30% by weight of HF, more preferentially more than 35% by weight of HF, in particular more than 40% by weight of HF, more particularly more than 45% by weight of HF, preferably less than 50% by weight of HF, based on the total weight of said liquid phase.

Preferably, said liquid phase A is a liquid phase low in HF. In particular, said liquid phase A comprises at least 10% by weight of 1,1,3,3-tetrachloropropene and/or 1,3,3,3-tetrachloropropene based on the total weight of said starting composition. Advantageously, said starting composition comprises at least 15% by weight of 1,1,3,3-tetrachloropropene and/or 1,3,3,3-tetrachloropropene, preferably at least 20% by weight of 1,1,3,3-tetrachloropropene and/or 1,3,3,3-tetrachloropropene, more preferentially at least 25% by weight of 1,1,3,3-tetrachloropropene and/or 1,3,3,3-tetrachloropropene, in particular at least 30% by weight of 1,1,3,3-tetrachloropropene and/or 1,3,3,3-tetrachloropropene, more particularly at least 35% by weight of 1,1,3,3-tetrachloropropene and/or 1,3,3,3-tetrachloropropene, favorably at least 40% by weight of 1,1,3,3-tetrachloropropene and/or 1,3,3,3-tetrachloropropene, advantageously favorably at least 45% by weight of 1,1,3,3-tetrachloropropene and/or 1,3,3,3-tetrachloropropene, preferentially favorably at least 50% by weight of 1,1,3,3-tetrachloropropene and/or 1,3,3,3-tetrachloropropene, and particularly favorably at least 55% by weight of 1,1,3,3-tetrachloropropene and/or 1,3,3,3-tetrachloropropene, based on the total weight of said liquid phase A.

Preferably, said liquid phase A comprises at least 60% by weight or at least 65% by weight or at least 70% by weight or at least 75% by weight or at least 80% by weight or at least 85% by weight or at least 90% by weight or at least 95% by weight or at least 99% by weight of 1,1,3,3-tetrachloropropene and/or 1,3,3,3-tetrachloropropene, based on the total weight of said liquid phase A.

Thus, the present process comprises step i) of providing a reactor comprising a cover, a bottom, sidewalls connecting said bottom and said cover, at least one reagent supply line and at least one line for drawing off the products formed, said reactor further containing a liquid phase A.

The stream B used in the present process comprises hydrofluoric acid. The term "hydrofluoric acid" used herein encompasses hydrofluoric acid and anhydrous hydrofluoric acid. Preferably, the hydrofluoric acid comprises less than 1000 ppm of water, advantageously less than 800 ppm of water, preferably less than 600 ppm, more preferentially less than 400 ppm of water, in particular less than 200 ppm of water, more particularly less than 100 ppm of water, preferably less than 50 ppm of water.

Preferably, the stream B comprises at least 50% by weight of hydrofluoric acid, advantageously at least 60% by weight of hydrofluoric acid, preferably at least 70% by weight of hydrofluoric acid, more preferentially at least 80% by weight of hydrofluoric acid, in particular at least 90% by weight of hydrofluoric acid, more particularly at least 95% by weight of hydrofluoric acid, preferably at least 99% by weight of hydrofluoric acid, based on the total weight of said stream B.

Preferably, the stream B is heated to a temperature T1 of from 100° C. to 170° C. The stream B is heated before it is introduced into said reactor. The heating of said stream B can be carried out by various means such as electrical tracing, i.e. the reagent supply line containing the stream B is coated with an electrical resistance, a heat exchanger or a jacket placed around the reagent supply line containing the stream B. The jacket contains a heat transfer fluid such as, for example, steam, pressurized hot water or oil.

The stream C used in the present process comprises 1,1,3,3-tetrachloropropene and/or 1,3,3,3-tetrachloropropene. Preferably, said stream comprises at least 50% by weight of 1,1,3,3-tetrachloropropene and/or 1,3,3,3-tetrachloropropene, advantageously at least 60% by weight of 1,1,3,3-tetrachloropropene and/or 1,3,3,3-tetrachloropropene, preferably at least 70% by weight of 1,1,3,3-tetrachloropropene and/or 1,3,3,3-tetrachloropropene, more preferentially at least 80% by weight of 1,1,3,3-tetrachloropropene and/or 1,3,3,3-tetrachloropropene, in particular at least 90% by weight of 1,1,3,3-tetrachloropropene and/or 1,3,3,3-tetrachloropropene, more particularly at least 95% by weight of 1,1,3,3-tetrachloropropene and/or 1,3,3,3-tetrachloropropene, preferably at least 99% by weight of 1,1,3,3-tetrachloropropene and/or 1,3,3,3-tetrachloropropene, based on the total weight of said stream C.

Said stream B and said stream C supplies said reactor via one or more reagent supply lines. Said stream B or said stream C may optionally be mixed before being introduced into said reactor. Said stream B and/or said stream C may optionally be injected into said liquid phase A present in said reactor.

Preferably, said streams B and C are brought into contact in the liquid phase. The reaction between hydrofluoric acid and 1,1,3,3-tetrachloropropene and/or 1,3,3,3-tetrachloropropene allows the formation of a stream D comprising trans-1-chloro-3,3,3-trifluoropropene. Preferably, the stream D is a gas stream.

Thus, the present invention provides a process for the production of trans-1-chloro-3,3,3-trifluoropropene comprising the steps of:

i) providing a reactor comprising a cover, a bottom, sidewalls connecting said bottom and said cover, at least one reagent supply line and at least one line for drawing off the products formed, said reactor further containing a liquid phase A;

ii) providing a stream B comprising hydrofluoric acid heated to a temperature T1 of from 100° C. to 170° C. and providing a stream C comprising 1,1,3,3-tetrachloropropene and/or 1,3,3,3-tetrachloropropene; said stream B and said stream C supplying said reactor via said at least one reagent supply line;

iii) reacting, in said liquid phase A, said stream B with said stream C in order to form a stream D comprising trans-1-chloro-3,3,3-trifluoropropene.

Preferably, step iii) is carried out at a temperature T2 of between 50° C. and 150° C., advantageously between 50° C. and 140° C., preferably between 50° C. and 130° C., more preferentially between 50° C. and 120° C., in particular between 50° C. and 110° C. More particularly, step iii) is carried out at a temperature T2 of between 60° C. and 105° C., preferably between 70° C. and 100° C., more preferentially between 80° C. and 100° C., in particular between 85° C. and 95° C., more particularly between 88° C. and 92° C.

According to one preferred embodiment, the temperature difference, in absolute value, between said temperature T1 and said temperature T2 is greater than or equal to 30° C. The temperature difference, in absolute value, between said temperature T1 and said temperature T2 may be greater than or equal to 32° C., or greater than or equal to 34° C., or greater than or equal to 36° C., or greater than or equal to 38° C., or greater than or equal to 40° C., or greater than or equal to 42° C., or greater than or equal to 44° C., or greater than or equal to 46° C., or greater than or equal to 48° C., or greater than or equal to 50° C.

Preferably, the temperature difference, in absolute value, between said temperature T1 and said temperature T2 is between 30° C. and 80° C., advantageously between 33° C. and 75° C., preferably between 35° C. and 70° C., in particular between 35° C. and 65° C., more particularly between 35° C. and 60° C.

According to one preferred embodiment, said reactor also comprises heating means capable of heating the liquid phase A. The heating means can heat the sidewalls of the reactor or the liquid phase A directly. For example, the heating means may be a double jacket placed around the sidewalls of the reactor, a coil placed in the reactor and in contact with said liquid phase A, or a recirculation loop with a heat exchanger, the latter being placed outside the reactor. The coil and the jacket contain a heat transfer fluid such as, for example, steam, pressurized hot water or oil. Said heating means make it possible to fix the temperature T3.

Preferably, said temperature T3 is higher than the temperature T2. In addition, said temperature T3 is less than 120° C., advantageously less than 115° C., preferably less than 110° C., more preferentially less than 105° C., in particular less than 100° C.

According to one preferred embodiment, said liquid phase A supplied in step i) is heated prior to the implementation of step iii) to a temperature T4 of between 50° C. and 150° C. Preferably, said liquid phase A is heated to a temperature T4 of between 50° C. and 140° C., preferably between 50° C. and 130° C., more preferentially between 50° C. and 120° C., in particular between 50° C. and 110° C. More particularly, said liquid phase A is heated to a temperature T4 of between 60° C. and 105° C., preferably between 70° C. and 100° C., more preferentially between 80° C. and 100° C., in particular between 85° C. and 95° C., more particularly between 88° C. and 92° C. In particular, said liquid phase A is heated to a temperature T4 equal to the temperature T2.

According to one preferred embodiment, the temperature T1 is between 120° C. and 170° C., advantageously between 125° C. and 165° C., preferably between 125° C. and 155° C.

According to a preferred embodiment, the temperature difference, in absolute value, between said temperature T3 and said temperature T2 is less than or equal to 30° C., in particular less than or equal to 25° C., more particularly less than or equal to 20° C.

Preferably, the temperature T1 is between 120° C. and 170° C., in particular between 125° C. and 165° C., more particularly between 125° C. and 155° C.; the temperature T2 is between 80° C. and 100° C., in particular between 85° C. and 95° C., more particularly between 88° C. and 92° C.; the temperature T3 is greater than T2 and less than 120° C., advantageously less than 115° C., preferably less than 110° C., more preferentially less than 105° C., in particular less than 100° C.; and the temperature T4 is between 80° C. and 100° C., in particular between 85° C. and 95° C., more particularly between 88° C. and 92° C.

In particular, the temperature T1 is between 120° C. and 170° C., in particular between 125° C. and 165° C., more particularly between 125° C. and 155° C.; the temperature T2 is between 80° C. and 100° C., in particular between 85° C. and 95° C., more particularly between 88° C. and 92° C.; the temperature T3 is greater than T2 and less than 120° C., advantageously less than 115° C., preferably less than 110° C., more preferentially less than 105° C., in particular less than 100° C.; the temperature T4 is between 80° C. and 100° C., in particular between 85° C. and 95° C., more particularly between 88° C. and 92° C.; and the temperature difference, in absolute value, between said temperature T3 and said temperature T2 is less than or equal to 30° C., in particular less than or equal to 25° C., more particularly less than or equal to 20° C.

More particularly, the temperature T1 is between 120° C. and 170° C., in particular between 125° C. and 165° C., more particularly between 125° C. and 155° C.; the temperature T2 is between 80° C. and 100° C., in particular between 85° C. and 95° C., more particularly between 88° C. and 92° C.; the temperature T3 is greater than T2 and less than 120° C., advantageously less than 115° C., preferably less than 110° C., more preferentially less than 105° C., in particular less than 100° C.; the temperature T4 is between 80° C. and 100° C., in particular between 85° C. and 95° C., more particularly between 88° C. and 92° C.; the temperature difference, in absolute value, between said temperature T3 and said temperature T2 is less than or equal to 30° C., in particular less than or equal to 25° C., more particularly less than or equal to 20° C.; and the temperature difference, in absolute value, between said temperature T1 and said temperature T2 is between 30° C. and 80° C., advantageously between 33° C. and 75° C., preferably between 35° C. and 70° C., in particular between 35° C. and 65° C., more particularly between 35° C. and 60° C.

Preferably, the temperature T1 is between 120° C. and 170° C., in particular between 125° C. and 165° C., more particularly between 125° C. and 155° C.; the temperature T2 is between 80° C. and 100° C., in particular between 85° C. and 95° C., more particularly between 88° C. and 92° C.; the temperature T3 is greater than T2 and less than 120° C., advantageously less than 115° C., preferably less than 110° C., more preferentially less than 105° C., in particular less than 100° C.; the temperature T4 is between 80° C. and 100° C., in particular between 85° C. and 95° C., more particularly between 88° C. and 92° C.; the temperature difference, in absolute value, between said temperature T3 and said temperature T2 is less than or equal to 30° C., in particular less than or equal to 25° C., more particularly less than or equal to 20° C.; the temperature difference, in absolute value, between said temperature T1 and said temperature T2 is between 30° C. and 80° C., advantageously between 33° C. and 75° C., preferably between 35° C. and 70° C., in particular between 35° C. and 65° C., more particularly between 35° C. and 60° C.; and the temperature T4 is equal to the temperature T2.

According to one preferred embodiment, said stream D also comprises at least one of the by-products selected from the group consisting of 1,1,1,3,3-pentafluoropropane, cis/trans-1,3,3,3-tetrafluoropropene and cis-1-chloro-3,3,3-trifluoropropene. Preferably, the total molar content of 1,1,1,3,3-pentafluoropropane, cis/trans-1,3,3,3-tetrafluoropropene and cis-1-chloro-3,3,3-trifluoropropene is less than 5 mol % in said stream D. In particular, the total molar content of 1,1,1,3,3-pentafluoropropane, cis/trans-1,3,3,3-tetrafluoropropene and cis-1-chloro-3,3,3-trifluoropropene is less than 4.9 mol % in said stream D. More particularly, the total molar content of 1,1,1,3,3-pentafluoropropane, cis/trans-1,3,3,3-tetrafluoropropene and cis-1-chloro-3,3,3-trifluoropropene is less than 4.8 mol % in said stream D. Preferably, the total molar content of 1,1,1,3,3-pentafluoropropane, cis/trans-1,3,3,3-tetrafluoropropene and cis-1-chloro-3,3,3-trifluoropropene is less than 4.7 mol % in said stream D. Advantageously preferably, the total molar content of 1,1,3,3-pentafluoropropane, cis/trans-1,3,3,3-tetrafluoropropene and cis-1-chloro-3,3,3-trifluoropropene is less than 4.6 mol % in said stream D. Preferentially preferably, the total molar content of 1,1,1,3,3-pentafluoropropane, cis/trans-1,3,3,3-tetrafluoropropene and cis-1-chloro-3,3,3-trifluoropropene is less than 4.5 mol % in said stream D. Particularly preferably, the total molar content of 1,1,1,3,3-pentafluoropropane, cis/trans-1,3,3,3-tetrafluoropropene and cis-1-chloro-3,3,3-trifluoropropene is less than 4.4 mol % in said stream D.

The molar content of trans-1-chloro-3,3,3-trifluoropropene in said stream D is greater than 95 mol %. Advantageously, the molar content of trans-1-chloro-3,3,3-trifluoropropene in said stream D is greater than 95.1 mol %. Preferably, the molar content of trans-1-chloro-3,3,3-trifluoropropene in said stream D is greater than 95.2 mol %. More preferentially, the molar content of trans-1-chloro-3,3,3-trifluoropropene in said stream D is greater than 95.3 mol %. In particular, preferably, the molar content of trans-1-chloro-3,3,3-trifluoropropene in said stream D is greater than 95.4 mol %. More particularly, the molar content of trans-1-chloro-3,3,3-trifluoropropene in said stream D is greater than 95.5 mol %. Preferably, the molar content of trans-1-chloro-3,3,3-trifluoropropene in said stream D is greater than 95.6 mol %. The molar contents are expressed on the basis of the organic compounds present in the stream considered.

The stream D may also comprise HCl and HF. The molar content mentioned above is that obtained at the outlet of the reactor, that is to say before purification.

Step i) is preferably carried out in the absence of catalyst.

Step i) may alternatively be carried out in the presence of a catalyst. The catalyst may be a $TiCl_4$ or $SbCl_5$ catalyst. The catalyst may also be an ionic liquid. The ionic liquids which may be suitable are Lewis acid derivatives based on aluminum, titanium, niobium, tantalum, tin, antimony, nickel, zinc or iron. The term "ionic liquids" refers to nonaqueous salts of ionic nature which are liquid at moderate temperatures (preferably below 120° C.). Ionic liquids preferably result from the reaction between an organic salt and an inorganic compound. Ionic liquids are preferably obtained by reaction of at least one halogen or oxyhalogen Lewis acid based on aluminum, titanium, niobium, tantalum, tin, antimony, nickel, zinc or iron with a salt of general formula $Y^+A^-$, wherein $A^-$ denotes a halide anion (bromide, iodide and, preferably, chloride or fluoride) or hexafluoroantimonate ($SbF_6^-$) and $Y^+$ a quaternary ammonium, quaternary phosphonium or ternary sulfonium cation. The halogen Lewis acid based on aluminum, titanium, niobium, tantalum, antimony, nickel, zinc or iron may be a chloro, bromo, fluoro or mixed derivative, for example a chlorofluoro acid. Mention may be made more particularly of the chlorides, fluorides or chlorofluorides having the following formulae:

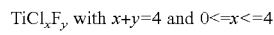
$TiCl_xF_y$ with $x+y=4$ and $0<=x<=4$

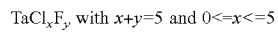
$TaCl_xF_y$ with $x+y=5$ and $0<=x<=5$

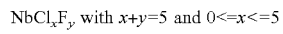
$NbCl_xF_y$ with $x+y=5$ and $0<=x<=5$

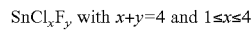
$SnCl_xF_y$ with $x+y=4$ and $1 \le x \le 4$

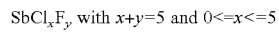
$SbCl_xF_y$ with $x+y=5$ and $0<=x<=5$

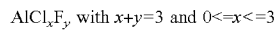
$AlCl_xF_y$ with $x+y=3$ and $0<=x<=3$

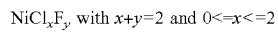
$NiCl_xF_y$ with $x+y=2$ and $0<=x<=2$

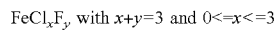
$FeCl_xF_y$ with $x+y=3$ and $0<=x<=3$

As examples of such compounds, mention may be made of the following compounds: $TiCl_4$, $TiF_4$, $TaCl_5$, $TaF_5$, $NbCl_5$, $NbF_5$, $SbCl_5$, $SbCl_4F$, $SbCl_3F_2$, $SbCl_2F_3$, $SbClF_4$, $SbF_5$, and mixtures thereof. The following compounds are preferentially used: $TiCl_4$, $TaCl_5+TaF_5$, $NbCl_5+NbF_5$, $SbCl_5$, $SbFCl_4$, $SbF_2Cl_3$, $SbF_3Cl_2$, $SbF_4Cl$, $SbF_5$, and $SbCl_5+SbF_5$. The antimony-based compounds are more particularly preferred. As examples of oxyhalogen Lewis acids that may be used according to the invention, mention may be made of $TiOCl_2$, $TiOF_2$ and $SbOCl_xF_y$ ($x+y=3$). In the salt $Y^+A^-$, the cation $Y^+$ may correspond to one of the following general formulae: $R^1R^2R^3R^4N^+$, $R^1R^2R^3R^4P^+$, $R^1R^2R^3S^+$ wherein the symbols $R^1$ to $R^4$, which are identical or different, each denote a saturated or unsaturated, cyclic or noncyclic, or aromatic hydrocarbyl, chlorohydrocarbyl, fluorohydrocarbyl, chlorofluorohydrocarbyl or fluorocarbyl group having from 1 to 10 carbon atoms, with one or more of these groups possibly also containing one or more heteroatoms such as N, P, S or O. The ammonium, phosphonium or sulfonium cation $Y^+$ may also form part of a saturated or unsaturated, or aromatic, heterocycle having from 1 to 3 nitrogen, phosphorus or sulfur atoms, and may correspond to one or other of the following general formulae:

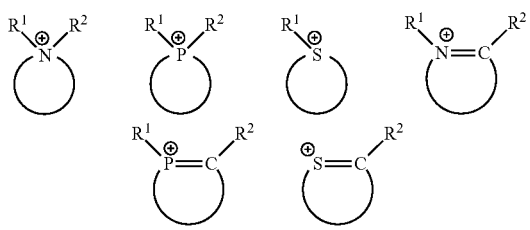

wherein $R^1$ and $R^2$ are as defined previously. A salt containing two or three ammonium, phosphonium or sulfonium sites in its formula may also be suitable for use. As examples of salts $Y^+A^-$, mention may be made of tetraalkylammonium chlorides and fluorides, tetraalkylphosphonium chlorides and fluorides, and trialkylsulfonium chlorides and fluorides, alkylpyridinium chlorides and fluorides, dialkylimidazolium chlorides, fluorides and bromides, and trialkylimidazolium chlorides and fluorides. Trimethylsulfonium fluoride or chloride, N-ethylpyridinium chloride or fluoride, N-butylpyridinium chloride or fluoride, 1-ethyl-3-methylimidazolium chloride or fluoride, and 1-butyl-3-methylimidazolium chloride or fluoride are more particularly valued. The ionic liquids may be prepared in a manner known per se by appropriate mixing of the halogen or oxyhalogen Lewis acid and the organic salt $Y^+A^-$. Reference may be made notably to the method described in document WO 01/81353. The catalyst may alternatively be triflic or trifluoroacetic acid as stated in U.S. Pat. No. 6,166,274.

Step iii) is preferably carried out at a pressure of 5 to 20 bara, preferably at a pressure of 10 to 18 bara, more particularly of 12 to 18 bara.

Preferably, the HF/[1,1,3,3-tetrachloropropene and/or 1,3,3,3-tetrachloropropene] molar ratio at the reactor inlet is between 5 and 10, more preferentially between 5 and 7, in particular between 5 and 6.

Said process preferably further comprises the steps of: (iv) at least one step of treating the stream D to give a stream E comprising E-1-chloro-3,3,3-trifluoropropene, HCl, HF and Z-1-chloro-3,3,3-trifluoropropene, and a stream F comprising primarily HF (for example at least 50% by weight, preferably at least 70% by weight, of HF); (v) at least one step of recovering the hydrochloric acid in the stream E, to give a stream G of HCl and a stream H comprising E-1-chloro-3,3,3-trifluoropropene, HCl, HF, and Z-1-chloro-3,3,3-trifluoropropene; (vi) at least one step of purifying the stream H obtained from step (v) to give E-1233zd, preferably with a purity of not less than 98%, advantageously not less than 99%, and very advantageously not less than 99.9% by weight.

Before the purification step, the stream H obtained in step (v) is preferably subjected to at least one separation step to give a flow comprising primarily HF (for example, at least 90% by weight, preferably at least 98% by weight, and advantageously at least 99% by weight of HF), which can be recycled to the reactor, and a flow comprising E-1-chloro-3,3,3-trifluoropropene, HCl, HF, and Z-1-chloro-3,3,3-trifluoropropene. The separation step is preferably a decantation, carried out at a temperature advantageously of between −50 and 50° C., preferably between −20° C. and 10° C.

The treatment step (iv) is preferably a reflux column, carried out advantageously at a temperature of between 30 and 120° C. to give the stream F, which is recycled to the reactor.

The recovery of HCl in step (v) is preferably obtained by means of a distillation column equipped with a bottom reboiler and a top reflux system. The temperature at the bottom is advantageously between 20 and 110° C. The temperature at the top is advantageously between −50 and 0° C. The distillation of HCl is typically performed at a pressure of between 7 and 25 bar.

According to one embodiment, the purification step (vi) preferably comprises at least one distillation step and advantageously at least two distillation steps. According to one preferred embodiment, the purification step (vi) comprises at least one step of washing with water and/or washing by means of a basic solution, a drying step, and at least one distillation step. The goal of this distillation step is to remove the light products and also the heavy products, which may be partly recycled to the reactor, depending on whether they are recyclable or not.

The process is preferably carried out continuously.

EXAMPLES

The apparatus used consists of a liquid phase reactor having a capacity of 60 liters with a jacket, made of 316L stainless steel. It possesses means for measuring temperature, pressure, and liquid level. The reagents can be supplied via a dip tube, while the products formed circulate through a 5 meter reflux column before being condensed overhead. This column is filled with a structured metal packing which allows the low-boiling-point products to be separated, while the raw material, the intermediate compounds and the unreacted HF drop back into the reactor. A pressure regulation valve imposes an operating pressure on the assembly. An in-line withdrawal system allows the flow of outgoing gas to be sampled, for which it is guided to a gas chromatograph. The reagents are supplied continuously, and the products are analyzed and collected continuously.

Example 1 (According to the Invention)

An amount of 25 liters of a liquid phase A comprising 1,1,3,3-tetrachloropropene is introduced into a reactor. The HF supply is preheated using a jacket supplied with superheated steam. The temperature T1 is 130° C. The liquid phase A is preheated to 90° C. using an electrical tracing, i.e. a temperature T4 of 90° C. The reactor jacket is then supplied with hot water using a boiler. The temperature T3 of the walls is 95° C. The reaction temperature T2, in this case the temperature of the liquid phase during the fluorination reaction, is 90° C. The pressure regulation is adjusted to 15 bara. The molar ratio between HF and 1,1,3,3-tetrachloropropene is 6. The gas stream composition results are given in table 1.

Example 2 (According to the Invention)

The procedure of example 1 is reproduced with a temperature of HF entering the reactor of 123° C. (T1). The temperature T3 is 97° C. The temperature T2 and the temperature T4 are 90° C. The reactor is heated in the same way as before. The molar ratio between HF and 1,1,3,3-tetrachloropropene is 6. The gas stream composition results are given in table 1.

Example 3 (Comparative)

The procedure of example 1 is reproduced with a temperature of HF entering the reactor of 117° C. (T1). The temperature T3 is 100° C. The temperature T2 and the temperature T4 are 90° C. The reactor is heated in the same way as before. The molar ratio between HF and 1,1,3,3-tetrachloropropene is 6. The gas stream composition results are given in table 1.

TABLE 1

|  | F1233zd-E (mol %) | F1233zdZ + F1234ze + 245fa (mol %) |
|---|---|---|
| Example 1 (Inv.) | 95.4 | 4.31 |
| Example 2 (Inv.) | 95.4 | 4.33 |
| Example 3 (Comp.) | 94.4 | 5.10 |

The values mentioned represent the molar content of the constituents mentioned in the gas stream obtained at the outlet of the reactor, the content is expressed on the basis of the organic compounds present in the reactor, that is to say without taking into account the HCl content and HF content in this stream.

The results detailed in table 1 demonstrate that the process according to the present invention generates fewer reaction by-products and overfluorinated products. The heating of the hydrofluoric acid combined with a control of the temperature of the reactor walls makes it possible to achieve a more efficient process for the production of trans-1-chloro-3,3,3-trifluoropropene.

The invention claimed is:

1. A process for the production of trans-1-chloro-3,3,3-trifluoropropene, comprising the steps of:
   i. providing a reactor comprising a cover, a bottom, sidewalls connecting said bottom and said cover, at least one reagent supply line and at least one line for drawing off the products formed, said reactor further containing a liquid phase A;
   ii. providing a stream B comprising hydrofluoric acid heated to a temperature T1 of from 100° C. to 170° C. and providing a stream C comprising 1,1,3,3-tetrachloropropene and/or 1,3,3,3-tetrachloropropene; said stream B and said stream C supplying said reactor via said at least one reagent supply line;
   iii. reacting, in liquid phase A, said stream B with said stream C in order to form a stream D comprising trans-1-chloro-3,3,3-trifluoropropene;
wherein step iii) is carried out at a temperature T2 of between 50° C. and 110° C., and the temperature difference, in absolute value, between temperature T1 and temperature T2 is greater than or equal to 30° C.

2. The process as claimed in claim 1, wherein said reactor also comprises heating means capable of heating said liquid phase A; the temperature of said heating means is the temperature T3; said temperature T3 is higher than the temperature T2 and said temperature T3 is less than 120° C.

3. The process as claimed in claim 1, wherein said liquid phase A provided in step i) is heated prior to the implementation of step iii) to a temperature T4 of between 50° C. and 110° C.

4. The process as claimed in claim 1, wherein said liquid phase A is a liquid phase low in HF.

5. The process as claimed in claim 4, wherein said liquid phase A low in HF is a liquid phase comprising less than 15% by weight of HF, based on the total weight of said liquid phase.

6. The process as claimed in claim 1, wherein the temperature T2 is between 60° C. and 105° C.

7. The process as claimed in claim 1, wherein the temperature T1 is between 120° C. and 170° C.

8. The process as claimed in claim 1, wherein the temperature T3 is less than 115° C.

9. The process as claimed in claim 1, wherein said stream D also comprises at least one of the by-products selected from the group consisting of 1,1,1,3,3-pentafluoropropane, cis/trans-1,3,3,3-tetrafluoropropene and cis-1-chloro-3,3,3-trifluoropropene; and the total molar content of said at least one of the by-products is less than 5 mol % in said stream D.

10. The process as claimed in claim 1, wherein the molar content of trans-1-chloro-3,3,3-trifluoropropene in said stream D is greater than 95 mol %.

11. The process as claimed in claim 1, wherein step iii) is carried out at a pressure of between 5 and 20 bara.

* * * * *